United States Patent [19]

Rygg

[11] 4,218,782
[45] Aug. 26, 1980

[54] HEART VALVE PROSTHESIS AND METHOD FOR THE PRODUCTION THEREOF

[75] Inventor: Inge H. Rygg, Charlottenlund, Denmark

[73] Assignee: Biocoating Anpartsselskab, Copenhagen, Denmark

[21] Appl. No.: 907,580

[22] Filed: May 19, 1978

[30] Foreign Application Priority Data

May 25, 1977 [DK] Denmark ............................ 2290/77

[51] Int. Cl.² ............................................... A61F 1/22
[52] U.S. Cl. ................................................. 3/1.5; 3/1
[58] Field of Search ................................. 3/1.5, 1.4, 1

[56] References Cited

U.S. PATENT DOCUMENTS

| | | | |
|---|---|---|---|
| 3,320,972 | 5/1967 | High et al. | 3/1.5 X |
| 3,548,418 | 12/1970 | Angell et al. | 3/1.5 |
| 3,744,062 | 7/1973 | Parsonnet | 3/1.5 |
| 3,755,823 | 9/1973 | Hancock | 3/1.5 |
| 3,974,526 | 8/1976 | Dardik et al. | 3/1.4 |
| 3,983,581 | 10/1976 | Angell et al. | 3/1.5 |
| 3,988,782 | 11/1976 | Dardik et al. | 3/1.4 X |

FOREIGN PATENT DOCUMENTS 492279  1/1976  U.S.S.R. ........................................ 3/1.5

OTHER PUBLICATIONS

"Fascia Lata Replacement of Aortic Valves", by Ake Senning et al., The Journal of Thoracic and Cardiovascular Surgery, vol. 54, No. 4, Oct. 1967, pp. 465–470.
"The Autologous Rectus Sheath Cardiac Valve", by C. L. Athanasuleas et al., The Journal of Thoracic & Cardiovascular Surgery, vol. 65, No. 1, Jan. 1973, pp. 118–123.

Primary Examiner—Ronald L. Frinks

[57] ABSTRACT

A flexible non-stented heart valve prosthesis made from a flat piece of a stabilized biological membrane. The membrane is folded along one or more folding lines and attached to a flat flexible non-biological base material so that one or more leaflets are formed. Preferably the membrane is pericardium and is attached by machine stitching to a woven polymeric base material. Different valve types including ventricular outflow patches and three-leaflet valves such as aortic valves and methods for their production are described.

The aortic valve is preferably made from three separate leaflets provided with narrow base materials serving as attachment margins which are stitched together in a manner to form a three-leaflet valve.

20 Claims, 9 Drawing Figures

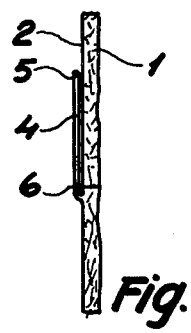
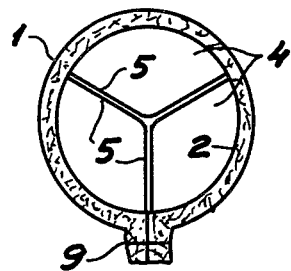
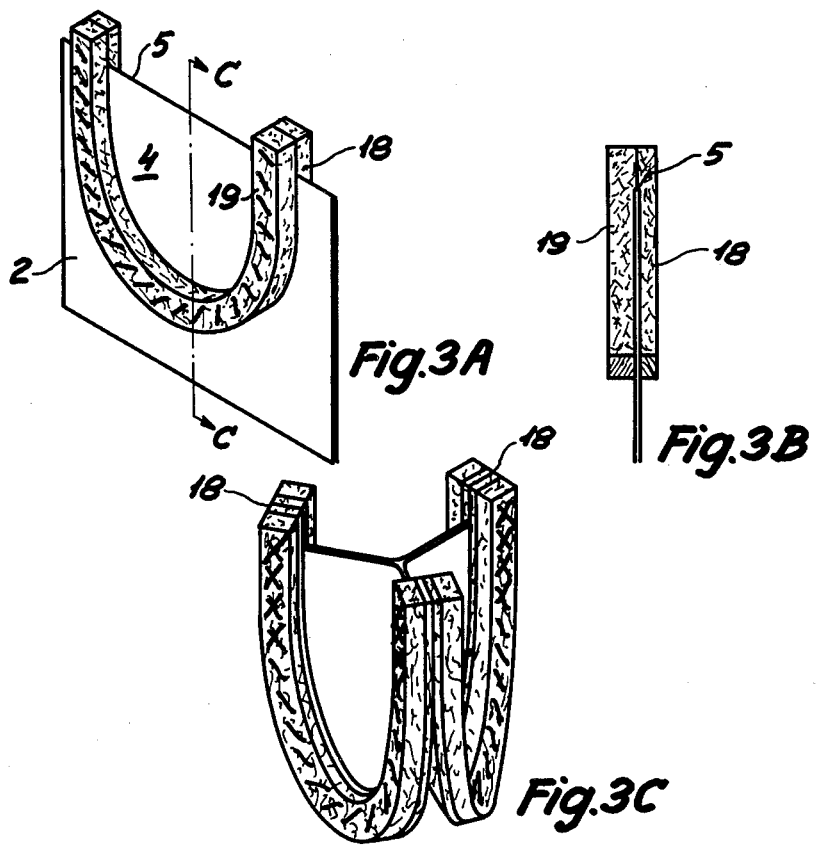

HEART VALVE PROSTHESIS AND METHOD FOR THE PRODUCTION THEREOF

BACKGROUND OF THE INVENTION

1. Field of the Invention

The present invention relates to a heart valve prosthesis on the basis of a stabilized biological membrane.

2. Description of the Invention

Heart valve prostheses produced from biological membranes have been known for many years. Fascia, pericardium, dura mater, ilium membranes and the like have been used. It has also been proposed to employ cut-out segments of vessels from umbilical cords for coating heart valves, cf. the U.S. Pat. No. 3,988,782.

Both fascia, pericardium and dura mater have been used in the human clinical medicine. A distinction must be made between membranes taken from the patient's own organism, the so-called autologous membranes, and membranes taken from other human beings (homologous membranes), or from animals (heterologous membranes). It has been found that heart valves produced from autologous membranes in contact with circulating blood undergo a specific reaction which is characteristic of a healing process. First, thick deposits of fibrin are formed on the membrane, and then a secondary cellular ingrowth takes place resulting in a thickening and shrinkage simultaneously with some degeneration of the encapsulated tissue. This process is progressive so that heart valves produced from autologous tissue cannot function in the long run.

The reaction of the organism to homologous and heterologous tissue is almost the opposite because the alien tissue has an immunologically different action so that the organism reacts with a kind of rejection reaction, which in this respect may be expedient. There are no fibrin coatings and no secondary cellular reaction apart from the region at the attachment margins. Heart valves produced from homologous or heterologous membranes therefore seem to remain unaffected, but it has been found that also the structure of the alient tissue tends to degenerate and degrade so that gradually the membranes weaken and break. At the same time the membranes tend to yield to pressure strains and expand. Attempts have been made to counteract this disadvantageous change in various manners by stabilizing the membranes with different tanning agents, preferably glutaraldehyde.

The membranes which are used today in the clinics are pericardium and dura mater. Considerable advantages are attached to constructing a heart valve from these membranes instead of utilizing the heretofore most used natural heart valves from animals or dead human beings. The rather difficult and laborious dissection of the heart valve itself is obviated and likewise the shaping and stabilizing of said valve in its naturally dilated state. Further, the valves of the patient as well as of the donor exhibit individual variations, and it is therefore a problem to find suitable sizes. Finally, the problems of suspending or attaching such a prosthesis in a form corresponding to its normal position are obviated. Thus, the use of a biological membrane results in a simplification of the production of the heart valves in several respects and also in a considerably better standardization. It further provides a greater choice of attachment methods, and finally it gives better possibilities of procuring suitable raw materials far more easily.

At present two types of such biological heart valve prostheses are available, one utilizes dissected natural heart valves, preferably from pigs, cf. for example the U.S. Pat. No. 3,548,418, No. 3,570,014, No. 3,755,823 and No. 3,983,581, the other is constructed from biological membranes, preferably porcine pericardium or dura mater. Both types are stabilized by tanning with glutaraldehyde and have the advantages in common that follow from the application of a heterologous material, viz. that they remain thin and movable, and that no deposits are formed on them that may get loose and cause thrombi. Compared with the existing mechanical valve prostheses, cf. for example the U.S. Pat. No. 3,325,827 and No. 3,396,409, they also have the advantages of a better hemodynamic, less hemolysis and no noise problems.

The drawbacks of the heretofore existing biological heart valve prostheses are, however, still that gradually the tissue will deteriorate in some degree in the form of decomposition or degradation of part of the tissue and possibly also wear. There is also a somewhat greater tendency to infection and consequently a greater strain on the material than in the mechanical prostheses. Particularly for the prostheses produced from heterologous biological membranes the weakness in the free margin of the valves is partly a consequence of the production method used up to now.

This type of prostheses are by and large produced by cutting a strip of the biological membrane. This strip is placed around and attached to a stent, which for example may bear a resemblance in appearance to that of the aforementioned U.S. Pat. No. 3,570,014 and which has three apexes between which the strip may be folded towards the centre and thus form a heart valve resembling a natural, three-leaflet valve, such as the aortic valve. The cutting of the strip invariably results in some damage to the margin of the membrane owing to the cutting of its constituents, in particular connective tissue fibrils. The free margin of the heart valve produced therefrom therefore becomes particularly vulnerable, and there is reason to believe that one of the late complications characteristic of this type of prostheses, viz. breaking transversely to the margin, is partly caused by this weakening of the tissue, stemming from the cutting. Furthermore, the suturing to the stent results inevitably in a certain damage of the biological material which is furthermore exposed to an abnormal stress at this suture line caused by the difference in consistency existing between the biological material and the more rigid stent. The stent also in itself exposes the biological material to an abnormal closing stress, giving a tendency to rupture of the free margin.

It is also characteristic of the two most used biological membranes, viz. pericardium and dura mater, that they are covered by a surface cell layer (the mesothelium) only on one side (the inside) and thus only have a microscopic, smooth, even surface on this side, while the other (the outside) is rough and uneven after the removal of fatty tissue and loose connective tissue. Consequently, the thickness and thereby also the strength of these membranes vary considerably.

The drawbacks of the rough side are further that bacteria can stick more easily thereto, and also a degradation or degeneration can take place more easily from this side.

To improve the quality of heart valve prostheses produced from a biological material researches have in recent years been carried out into an improvement of the preservation of the tissue, which has lead to a method of impregnating and/or coating biological tissue with polymeric materials, cf. the Danish patent application No. 1690/76, corresponding to U.S. application Ser. No. 784,916 filed Apr. 5, 1977 and which is incorporated herein by reference.

These prostheses on the basis of impregnated and/or coated heart valves exhibit considerable advantages compared with mechanical valves as well as valves of the type described above, where for example a porcine valve is attached to a stent, and they do not suffer from the problems which are observed in valves on the basis of biological membranes and which stem from the damaged marginal regions.

However, said Danish application does not obviate the problems relating to the dissection of the heart valve and the placing thereof in its genuine normal position in the patient.

The object of the present invention is to provide a flexible non-stented heart valve prosthesis which has the advantages known from the use of biological membranes without being encumbered with the known drawbacks. This object is achieved by the prosthesis of the invention which is characterized in that a flat piece of a stabilized biological membrane is folded along one or more folding lines and attached to a flat flexible non-biological base material to form one or more leaflets. The biological membrane is stabilized before or after the folding and forming of the leaflets. The most expedient manner of attaching the strip to the base material is by stitching, however, also gluing or a combination of stitching and gluing may be used. Special importance has been attached to the development of a production method which permits machine stitching with the consequent advantages in terms of production. Machine stitching thus makes possible a more accurate, uniform and reproducable stitching, the use of various types of stitches, and also the use of a reinforced suture.

In an embodiment of the prosthesis of the invention the impregnation and/or coating principle described in application No. 1690/76 is utilized because this results in a reinforcement of the membrane. If the biological membrane is of the type which on one side has mesothelial cells it is preferred to impregnate and/or coat from the other side to keep the mesothelial cells intact.

The invention also relates to a method of producing the subject prostheses, and the method of the invention is characterized by folding a flat piece of a biological membrane along one or more folding lines and stitching the strip on a flexible nonbiological base material to form one or more leaflets. Said stitching is preferably effected by machine.

The biological membrane is preferably porcine pericardium because it is easily available and also because it has a thickness suitable for the purpose, but any other thin biological membrane may be used, preferably with one side coated with mesothelial cells.

The base material is preferably a flexible polymeric material, such as a polyester, which is advantageously woven or crocheted so that it is easy to stitch.

In the production the membrane is folded so that the smooth cell clad side faces outwardly. Several advantages are achieved hereby:

1. The produced valve consists of a double layer of membrane.
2. There is a smooth surface layer cell coating on both sides of the valve.
3. The free edge of the heart valve is constituted by an undamaged membrane.
4. As mentioned, a reinforcement of the membrane can be achieved by impregnating and/or coating the rough side with polymeric materials prior to the folding.
5. A further reinforcement can be achieved for example by inserting another suitable material between the two layers prior to the folding, for example polymeric materials, such as polyesters, arranged in parallel.
6. Neither the impregnation and/or coating material nor the reinforcement material is in direct contact with the circulating blood, for which reason it is not specically required that the materials be non-thrombogenic.

In connection with the folding the membrane may be stretched in the direction of the pleat before or during the stabilization and cross-linking known per se of the biological membrane with for example glutaraldehyde. This gives several advantages:

1. A considerable increase in the strength of the membrane is achieved because after the stabilization the orientation of the fibrils resulting from the stretching is maintained.
2. Decreased tendency to subsequent elongation in the stretching direction and thus change of the shape of the valve.
3. Greater uniformity between the biological and non-biological materials of the valve as regards expansion.

Prostheses of the invention are firstly the so-called valved right ventricular outflow patch which is used as a ceiling on a longitudinal incision over the outflow patch from the right ventricle out on the pulmonary artery in case of narrowings at this point, and where the valve prevents the blood from running back to the ventricle.

The invention further comprises prostheses with several, usually three, leaflets to replace the heart valves, such as the aortic valve, the valve of the pulmonary artery and the mitral and tricuspid valves. In the production of the three-leaflet valve prostheses the prosthesis may be given the shape of a tube for example after the folding and forming of the three leaflets, which tube may be circular or have any other desired cross section, such as oval or triangular, the marginal regions being joined, preferably by stitching.

Especially in the production of aortic valve prostheses of the invention it is preferred to form the base material as a narrow tape-shaped attachment margin which is attached, particularly by machine stitching and optionally by gluing in the form of two tapes on either side of a length of a folded biological membrane. When the portion of the membrane is removed that is disposed outside the attachment margin, a tongue-shaped leaflet is obtained. By stitching together three such leaflets in pairs along a section of their attachment margins, a flexible non-stented aortic valve prosthesis with flexible attachment margins is achieved which contrary to the above-mentioned known prostheses where the leaflets are attached to a stent, are not exposed to the above-mentioned abnormal stresses.

BRIEF DESCRIPTION OF THE DRAWINGS

The invention is illustrated in more detail in the drawing in which

FIG. 2B is a sectional view taken along the line B—B of FIG. 2A, and FIG. 2C shows the prosthesis after the shaping to a tube, and FIGS. 3A, 3B and 3C show an embodiment of an aortic valve prosthesis. FIG. 3A shows the formation of a single leaflet, FIG. 3B is a sectional view taken along the line C—C of FIG. 3A, while FIG. 3C shows the finished prosthesis composed of the three leaflets shown in FIG. 3A.

In FIGS. 1 A-C is shown the non-biological base material 1 which for example may be a vascular prosthesis material of woven polyester. The biological membrane 2, which for example is porcine pericardium whose mesothelial side faces outwardly, is attached by longitudinal stitches 3 to said base material. The membrane is folded along two folding lines so as to form a pleat with an undamaged free upper edge 5. The bottom of the pleat is provided with a transverse stitch 6, and an arcuate stitch 7 has been effected to form the leaflet 4 having the shape of a pocket. After said stitchings the shape shown in FIG. 1B is imparted to the prosthesis. Before or after the placing on the base the membrane is subjected to a stabilization treatment, for example with glutaraldehyde. If desired, the membrane may be pre-impregnated and/or precoated with a polymeric material and reinforcement filaments of a polymeric material may be preinserted between the two portions of the membrane forming the leaflet 4.

A three-leaflet heart valve is shown in FIGS. 2A-2C in which the same reference numerals are used as in FIGS. 1A-C for the same details.

Figure 1A:
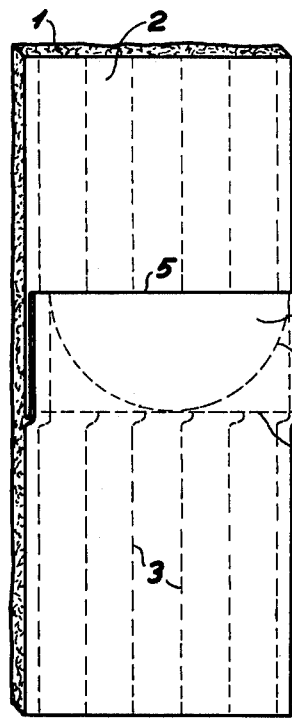
FIGS. 1A, 1B and 1C show an embodiment of a valved right ventricular outflow patch, FIG. 1A being a front view of the prosthesis prior to the shaping, FIG. 1B showing the prosthesis in the shape suitable for implantation and FIG. 1C being a section taken along the line A—A of FIG. 1B, FIGS. 2A, 2B and 2C show an embodiment of a three-leaflet heart valve prosthesis, for example to replace the valve of the pulmonary artery.
Figure 1B:
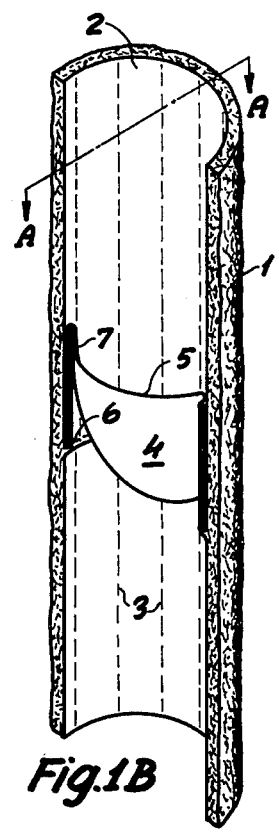
Figure 1C:
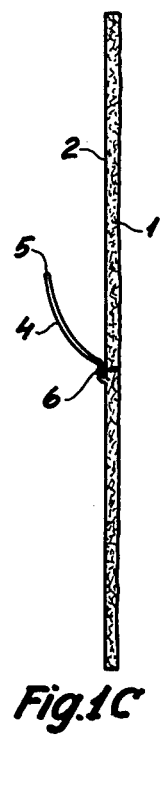
Figure 2A:
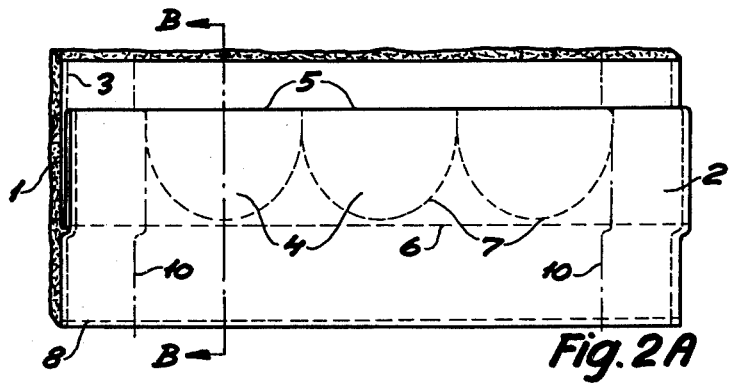
FIG. 2A is a front view of the prosthesis prior to the shaping.

The base material is here a strip of rather firmly woven polymeric material, for example a material of polyester (Dacron), to which the biological membrane 2 is stitched with stitches 3, 6 and 8 after having been folded to a pleat. The arcuate stitches 7 define three leaflets 4 having free upper edges 5.

The folding and stitching 9 of the strip along line 10 to form a tube brings about a three-leaflet valve disposed within the tube which thus outwardly consists of the woven material and inwardly of the biological membrane. After the stitching the tube is shaped, and the leaflets are dilated by suitable tools, whereupon a stabilization treatment is carried out, for example with glutaraldehyde. A stabilization including stretching may also be carried out in advance. Here too, the valves may, if desired, be impregnated and/or coated and/or reinforced with polymeric materials as explained above.

FIGS. 3A-3C show a preferred embodiment of an aortic valve prosthesis, having a structure of three separate leaflets attached to a base material serving as an attachment margin. FIG. 3A shows the folded preferably prestabilized biological membrane 2 with the undamaged upper edge 5. On this is stitched the base material in the form of a thin subjacent tape 18 and a somewhat thicker superjacent tape 19. The excess membrane is then cut off, and a tongue-shaped leaflet 4 is obtained.

FIG. 3B is a sectional view taken along the line C—C of FIG. 3A, showing the undamaged upper edge 5 and the two tapes 18 and 19.

In FIG. 3C the three tongue-shaped leaflets are sutured together in pairs along a section of the tapes 18 arranged against each other. The leaflets may then be dilated by suitable tools and the tapes 19 permit a suturing of the prosthesis to replace the defective valve without damaging the leaflets.

What I claim is:

1. A heart valve prosthesis made from a flat strip piece of a stabilized biological membrane which is folded along at least one folding line to form opposed layers and attached to a flat flexible non-biological base material to form at least one leaflet.

2. The heart valve prosthesis according to claim 1, wherein the strip is attached by stitching.

3. A heart valve prosthesis according to claim 2, wherein the strip is attached by machine stitching.

4. The heart valve prosthesis according to claim 1, wherein a biological membrane having on one side a mesothelial layer, is attached so that the non-mesothelial side faces the base material.

5. The heart valve prosthesis according to claim 1, wherein the non-biological base material is a flexible polymeric material.

6. The heart valve prosthesis according to claim 5, wherein the polymeric material is a woven material.

7. The heart valve prosthesis according to claim 1, wherein the biological membrane is porcine pericardium.

8. The heart valve prosthesis according to claim 1, wherein the biological membrane is provided with a reinforcement at least in the region forming the leaflet or leaflets.

9. The heart valve prosthesis according to claim 8, wherein said reinforcement is provided by impregnating the biological membrane with a physiologically compatible polymeric material.

10. The heart valve prosthesis according to claim 4, wherein the biological membrane is reinforced by impregnating from the non-mesothelial side.

11. The heart valve prosthesis according to claim 8, wherein said reinforcement is provided by inserting a polymeric material, between the two layers of biological membrane forming the leaflet or leaflets.

12. The heart valve prosthesis according to claim 11, wherein said reinforcing polymeric material is in the form of filaments.

13. The heart valve prosthesis according to claim 1, wherein at least in the region forming the leaflets the strip is stretched in the folding direction prior to the placing on the base material.

14. The heart valve prosthesis according to claim 1, wherein the strip of biological membrane after the folding and the formation of at least one leaflet is shaped to a tube, the longitudinal axis of which is disposed substantially perpendicularly to the folding lines.

15. A heart valve prosthesis according to claim 1 for use as an aortic valve prosthesis comprising three tongue-shaped leaflets each of which being formed by folding a strip of a biological membrane along a folding line, attaching on either side a narrow tape-shaped base material of a flexible nonbiological material serving as attachment margins, removing the portion of the membrane located outside the attachment margins and stitching together said leaflets in pairs along a section of the attachment margins to form a three-leaflet valve.

16. A method of producing a heart valve prosthesis comprising the steps of folding a flat strip piece of biological membrane along at least one folding line to form opposed layers and stitching the strip on a flat flexible non-biological base material to form at least one leaflet.

17. The method according to claim 16 comprising the steps of folding the strip along two parallel folding lines, stitching the strip on the base material, forming three leaflets and further stitching the marginal regions together in order to form a tube the longitudinal axis of which is disposed substantially perpendicularly to the folding lines.

18. A method of producing an aortic valve prosthesis comprising the steps of folding a strip of a biological membrane along a folding line, stitching a tongue-shaped attachment margin of a tape-shaped flexible non-biological material to either side of the membrane, removing the excess portion of the membrane, stitching the obtained tongue-shaped leaflet together with two leaflets produced in the same manner along a section of the respective attachment margins to form a three-leaflet valve.

19. The heart valve prosthesis according to claim 5, wherein the polymeric material is a crocheted material.

20. The heart valve prosthesis according to claim 1, wherein the biological membrane is calf pericardium.

* * * * *